US009381310B2

(12) United States Patent
Iwase et al.

(10) Patent No.: US 9,381,310 B2
(45) Date of Patent: Jul. 5, 2016

(54) INJECTION NEEDLE ASSEMBLY AND DRUG INJECTION APPARATUS

(75) Inventors: Yoichiro Iwase, Ashigarakami-gun (JP); Takayuki Yokota, Nakakoma-gun (JP); Yoshinori Hishikawa, Nakakoma-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 989 days.

(21) Appl. No.: 13/579,837
(22) PCT Filed: Feb. 10, 2011
(86) PCT No.: PCT/JP2011/052873
§ 371 (c)(1), (2), (4) Date: Aug. 17, 2012
(87) PCT Pub. No.: WO2011/111469
PCT Pub. Date: Sep. 15, 2011

(65) Prior Publication Data
US 2012/0323187 A1  Dec. 20, 2012

(30) Foreign Application Priority Data
Mar. 10, 2010  (JP) ................................. 2010-053832

(51) Int. Cl.
*A61M 5/32*  (2006.01)
*A61M 5/46*  (2006.01)
(Continued)

(52) U.S. Cl.
CPC ............... *A61M 5/46* (2013.01); *A61J 1/2096* (2013.01); *A61M 5/19* (2013.01); *A61M 5/24* (2013.01);
(Continued)

(58) Field of Classification Search
CPC ........... A61M 5/24; A61M 5/32; A61M 5/34; A61M 5/46; A61M 5/1407–5/1409; A61M 5/1413; A61M 5/158; A61M 5/162; A61M 5/19; A61M 5/204; A61M 5/2066; A61M 5/2448; A61M 5/2466; A61M 5/284; A61M 5/288; A61M 5/3146; A61M 5/3294; A61M 5/3297; A61M 2005/1587; A61M 2005/1787; A61M 39/14; A61J 1/20; A61J 1/2089; A61J 1/2096
See application file for complete search history.

(56) References Cited

U.S. PATENT DOCUMENTS 1,274,081 A * 7/1918 Riethmueller ................. 604/117
1,511,827 A * 10/1924 Comer .................... A61M 5/28
604/192
(Continued)

FOREIGN PATENT DOCUMENTS

JP  57-45946  9/1955
JP  57-45946  3/1982
(Continued)

OTHER PUBLICATIONS

International Search Report (PCT/ISA/210) issued on Mar. 8, 2011, by the Japanese Patent Office as the International Searching Authority for International Application No. PCT/JP2011/052873.
(Continued)

*Primary Examiner* — Bhisma Mehta
*Assistant Examiner* — Larry R Wilson
(74) *Attorney, Agent, or Firm* — Buchanan Ingersoll & Rooney PC

(57) ABSTRACT

An injection needle assembly is an assembly used by being attached to an injector including an injection barrel filled with medicine and a needle tube, and is provided with a sticking needle tube having a needle tip to be stuck into a skin, a needle holding portion, an engagement portion and a connection portion. The needle holding portion holds the sticking needle tube and a fit tube of the engagement portion is engaged with a needle hub of the injection barrel. The connection portion includes a luminal portion in which there are arranged a proximal end on the opposite side of the needle tip of the sticking needle tube and a needle tip (ejection port) at the needle tube of the injector, and the sticking needle tube and the needle tube communicate with each other in a liquid tight manner.

19 Claims, 7 Drawing Sheets

(51) Int. Cl.
  *A61M 5/19*  (2006.01)
  *A61M 5/24*  (2006.01)
  *A61M 5/28*  (2006.01)
  *A61J 1/20*  (2006.01)
  *A61M 5/34*  (2006.01)
  *A61M 5/14*  (2006.01)

(52) U.S. Cl.
  CPC ........... *A61M 5/2448* (2013.01); *A61M 5/2466* (2013.01); *A61M 5/284* (2013.01); *A61M 5/288* (2013.01); *A61M 5/32* (2013.01); *A61M 5/3294* (2013.01); *A61M 5/3297* (2013.01); *A61M 5/34* (2013.01); *A61M 5/1409* (2013.01)

(56) References Cited

U.S. PATENT DOCUMENTS

| | | | | |
|---|---|---|---|---|
| 2,752,919 | A * | 7/1956 | Gabriel | A61M 5/32 604/240 |
| 4,409,991 | A | 10/1983 | Eldridge | |
| 5,626,567 | A | 5/1997 | Gmeiner | |
| 2003/0050602 | A1 | 3/2003 | Pettis et al. | |
| 2003/0236501 | A1 * | 12/2003 | Donnan et al. | 604/192 |
| 2006/0229562 | A1 | 10/2006 | Marsh et al. | |
| 2007/0060904 | A1 | 3/2007 | Vedrine et al. | |
| 2008/0033395 | A1 * | 2/2008 | Alchas | 604/506 |

FOREIGN PATENT DOCUMENTS

| | | |
|---|---|---|
| JP | 8-168530 A | 7/1996 |
| JP | 2000-37456 A | 2/2000 |
| JP | 2001-137343 A | 5/2001 |
| JP | 2005-527249 A | 9/2005 |
| JP | 2008-532701 A | 8/2008 |
| WO | WO 03/022330 A2 | 3/2003 |

OTHER PUBLICATIONS

Extended European Search Report dated Apr. 4, 2014, issued by the European Patent Office in the corresponding European Application No. 11753131.9. (5 pages).

Japanese Office Action issued May 19, 2015, by the Japan Patent Office, in corresponding Japanese Patent Application No. 2012-504372 with English translation of Office Action (6 pages).

* cited by examiner

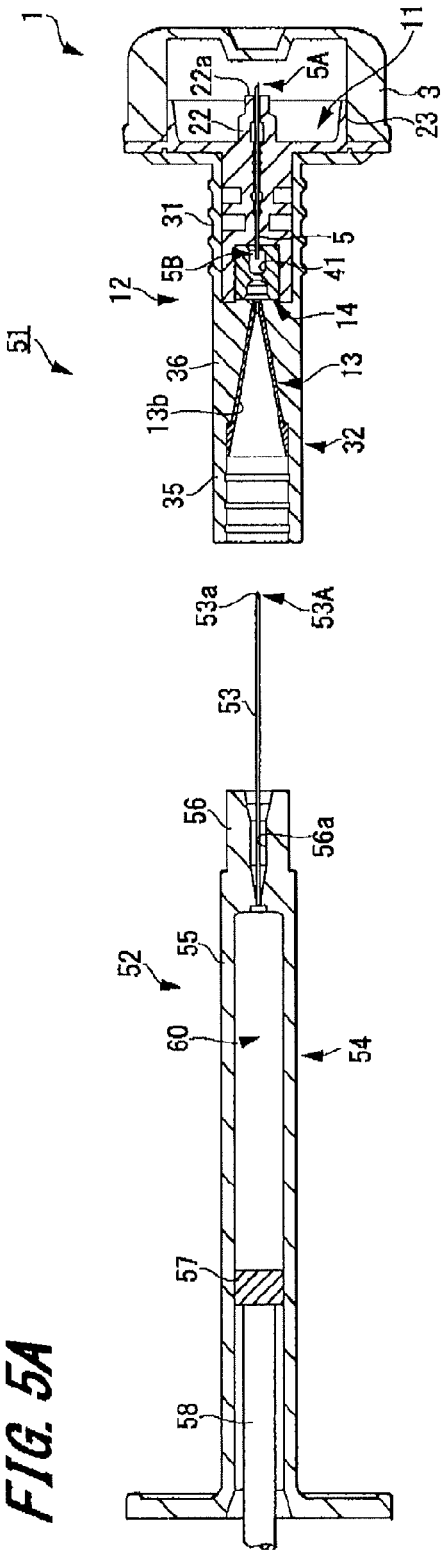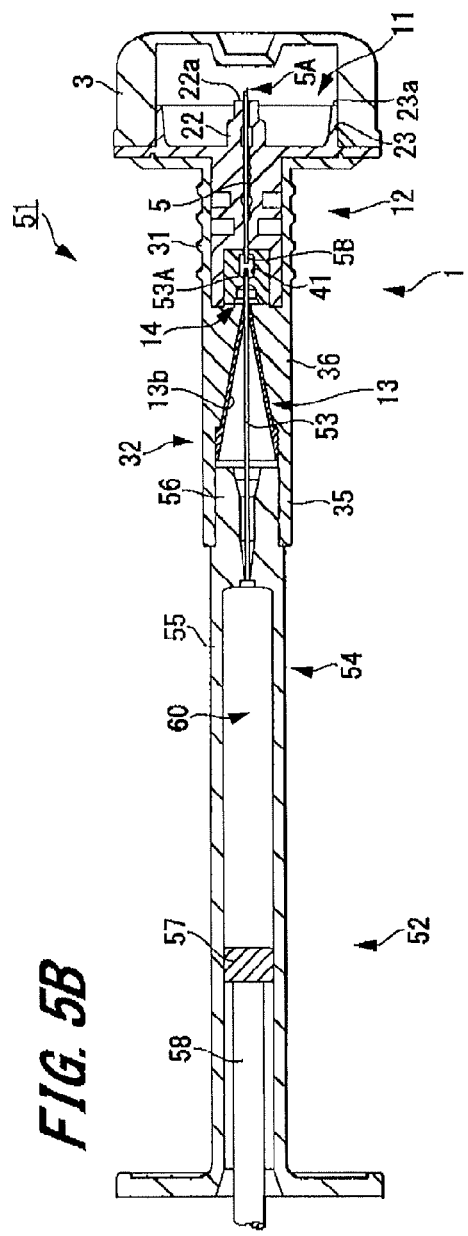

INJECTION NEEDLE ASSEMBLY AND DRUG INJECTION APPARATUS

TECHNICAL FIELD

The present invention relates to an injection needle assembly and a medicine injection apparatus used for sticking a needle tip from a surface of a skin and for injecting medicine into an upper layer region of the skin.

BACKGROUND ART

In recent years, there was reported an article that an immune obtaining response equivalent to a hypodemic administration and a muscle administration can be obtained by administering influenza vaccine in a situation of making an upper layer region of a skin where a lot of immunocompetent cells exist as a target region even if the applied dose is reduced. Therefore, it is possible to reduce the applied dose by administering the influenza vaccine into an upper layer region of a skin, so that there is a possibility that more people can be inoculated with the influenza vaccine. Note that the wording "upper layer region of the skin" indicates "epidemis" and "dermis" within the skin.

As an administration method of medicine to an upper layer region of a skin, there have been known methods using a single needle, multiple needles, a patch, gas and the like. Then, when taking stability, reliability and manufacturing cost of the administration into account, the method using a single needle is the most suitable as the administration method to the upper layer region of the skin. As a method of administering vaccine to an upper layer region of a skin by using this single needle, there has been known a Mantoux method from old times. The Mantoux method is a method in which medicine of around 100 µL is administered by inserting a needle having a needle tip of short bevel with a size of generally 26 to 27 gauge by an amount of around 2 mm to 5 mm from an oblique direction of around 10° to 15° with respect to the skin.

However, in the Mantoux method, the procedure thereof is difficult, and the procedure is left up to the skill of a doctor who carries out the injection. In particular, there is a possibility that an infant may move at the time of administration, so that it is difficult to administer influenza vaccine by the Mantoux method. Therefore, there is required development of a device which can easily administer vaccine at the upper layer region of the skin.

In Patent Document 1, there is described an injection apparatus in which a limiter having a skin contact surface is connected to a needle hub of an injector. The limiter of the injection apparatus described in this Patent Document 1 is formed in a tubular shape covering the periphery of the needle tube and includes a skin contact surface from which the injection needle protrudes. This limiter restricts the length of the injection needle (protrusion length) protruding from the skin contact surface to the range of 0.5 mm to 3.0 mm and the medicine injected from the injection needle is made to be administered into the inside of the skin.

Also, In Patent Document 2, there is described an apparatus relating to a sticking adjuster for an injection needle and an injection needle assembly provided with that adjuster which prevent the injection needle from being stuck more deeply than an aimed depth. Within the sticking adjusters for injection needles disclosed in this Patent Document 2, there exists a sticking adjuster for an injection needle which closely-contacts with the periphery of the injection needle and which includes a skin contact surface.

Meanwhile, it sometimes happens that an injector is used by sucking-in medicine from a vial. The vial is a medicine storage container in which medicine can be preserved for an extended time in a liquid or freeze-dried state. An opening portion of this vial is normally sealed with a rubber stopper having a thickness of 3 mm to 5 mm. This rubber stopper is designed such that it does not permit leakage of the medicine therethrough even when it is repeatedly pierced by a needle tube. Therefore, most of vaccines, which are used often for group vaccination, are sucked-in from vials.

The limiter described in the Patent Document 1 and the sticking adjuster for the injection needle described in the Patent Document 2 are constituted so as to include an injection needle having a shortened protrusion length (for example, 0.5 mm to 3.0 mm) such that medicine can be administered at the upper layer region of the skin. Therefore, it becomes impossible for the injection needle to pass through the rubber stopper of the vial and it was not possible to use it in the way of sucking-in medicine from the vial.

For example, if it is before attaching the limiter disclosed in the Patent Document 1 to the needle hub of the injector, it is possible to suck-in medicine from the vial by using the injector. Also, if it is before attaching the sticking adjuster for the injection needle disclosed in the Patent Document 2 to the injector, it is possible to suck-in medicine from the vial by using the injector.

PRIOR-ART DOCUMENT

Patent Document

Patent Document 1: Japanese unexamined patent publication No. 2001-137343
Patent Document 2: Japanese unexamined patent publication No. 2000-37456

DISCLOSURE OF THE INVENTION

Problem to be Solved by the Invention

However, in case of attaching the limiter disclosed in the Patent Document 1 to the injector after the medicine is sucked-in from the vial, it happens that the attachment thereof will be carried out by the user. At that time, it is difficult to insert the injection needle of the injector into the opening of the limiter and it happens that the attachment work becomes complicated. Also, even in a case in which the attachment of the sticking adjuster for an injection needle disclosed in the Patent Document 2 to the injection needle is to be carried out, it is difficult to insert the injection needle into a hole (25a) of a sticking adjuster for an injection needle (22a) and it happens that the attachment work becomes complicated.

Further, in these cases, it is conceivable that the needle tip is to be bent by touching the limiter and/or a wall of the sticking adjuster for the injection needle at a time of attachment thereof. Also, in a case in which the limiter or the like is formed from plastic, it is conceivable that the limiter or the like may be stuck by the needle tip.

Also, there was a possibility with respect to the injection needle passed through the rubber stopper of the vial that the needle tip thereof may be squashed. Therefore, when using an injection needle passed through the rubber stopper for sticking into the skin, there was such a problem that the pains occurring at a time of sticking and at a time of the medicine administration will increase. Further, when the needle tip is squashed, it becomes difficult to position the needle tip thereof at the upper layer region of the skin and there was such a problem that the medicine may leak from the upper layer of the skin.

The present invention was invented in view of such a situation and has an object to provide an injection needle assembly and a medicine injection apparatus using the injection needle assembly thereof, to which an injector mounted with a needle tube can be connected easily.

Means for Solving the Problem

An injection needle assembly of the present invention is used by being attached to an injector including an injection barrel filled with medicine and a needle tube and is provided with a sticking needle tube having a needle tip to be stuck into a skin, a needle holding portion, an engagement portion, and a connection portion. The needle holding portion holds the sticking needle tube, and the engagement portion is engaged with the injection barrel. The connection portion includes a luminal portion at which there are arranged a proximal end opposite to the needle tip of the sticking needle tube and an ejection port in the needle tube of the injector and communicates the sticking needle tube and the needle tube with each other in a liquid tight manner.

A medicine injection apparatus of the present invention is provided with an injector including an injection barrel filled with medicine and a needle tube, and an injection needle assembly attached to the injector. The injection needle assembly of this medicine injection apparatus includes a sticking needle tube having a needle tip to be stuck into a skin, a needle holding portion, an engagement portion, and a connection portion. A needle holding portion of the injection needle assembly holds the sticking needle tube, and the engagement portion is engaged with the injection barrel. The connection portion includes a luminal portion at which there are arranged a proximal end opposite to the needle tip of the sticking needle tube and an ejection port in the needle tube of the injector and communicates the sticking needle tube and the needle tube with each other in a liquid tight manner.

In case of attaching an injection needle assembly of the present invention to an injector, an engagement portion of the injection needle assembly is engaged with an injection barrel of the injector. Thus, the ejection port in the needle tube of the injector is inserted into the connection portion and arranged at the luminal portion. At this luminal portion, there is arranged the proximal end of the sticking needle tube which is held at the needle holding portion. Therefore, the sticking needle tube and the needle tube of the injector communicate with each other in a liquid tight manner by means of the connection member, and it is possible to eject the medicine filled in the injection barrel from the sticking needle tube.

Effect of the Invention

According to the injection needle assembly and the medicine injection apparatus of the present invention, it is possible to easily connect the injector mounted with the needle tube and it is possible to eject the medicine filled in the injection barrel from the sticking needle tube.

BRIEF DESCRIPTION OF DRAWINGS

FIG. 5A is an explanatory view of a state immediately before attaching the first exemplified embodiment of the injection needle assembly of the present invention to an injector;

FIG. 5B is an explanatory view of a state of attaching the injection needle assembly to the injector;

MODE FOR CARRYING OUT THE INVENTION

Figure 1:
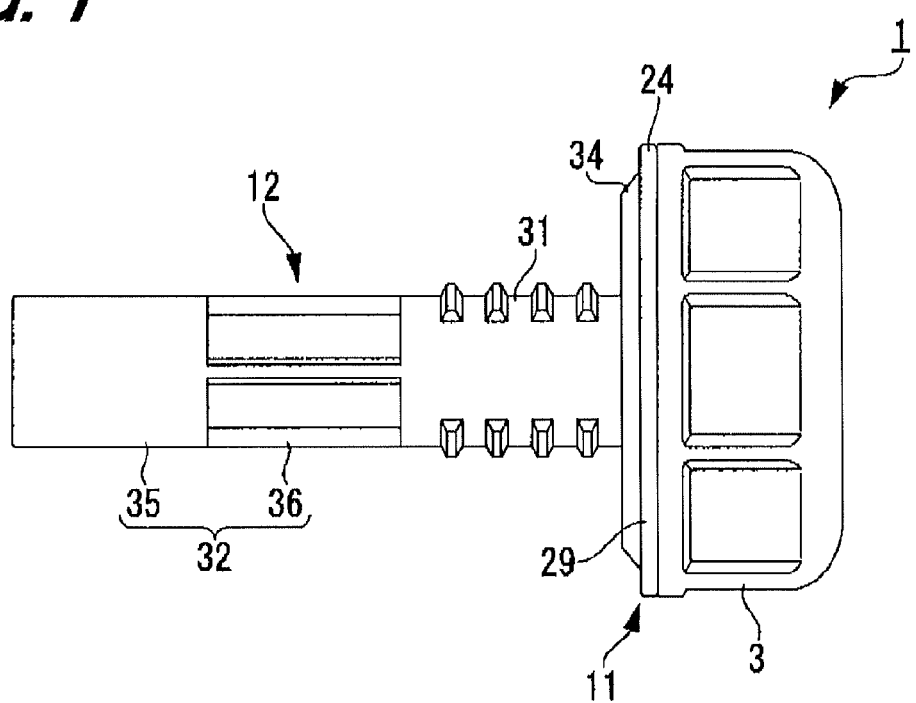
FIG. 1 is a side view of a first exemplified embodiment of an injection needle assembly of the present invention.

Hereinafter, there will be explained embodiments for practicing an injection needle assembly and a medicine injection apparatus of the present invention with reference to FIG. 1 to FIG. 7. Note in each drawing that the same reference numerals are applied for the common members.

1. First Exemplified Embodiment

Injection Needle Assembly

First, there will be explained a first exemplified embodiment of an injection needle assembly of the present invention with reference to FIG. 1 to FIG. 4.

Figure 2:
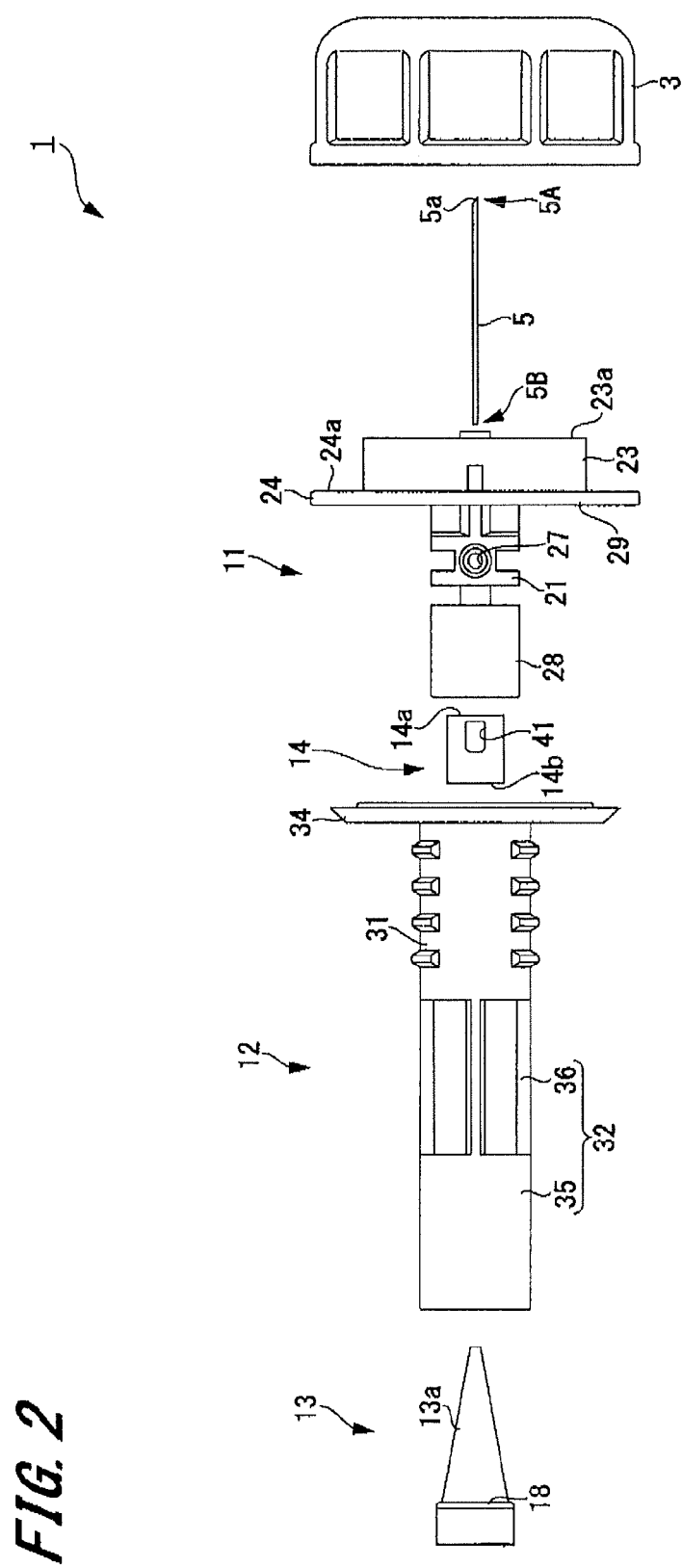
FIG. 2 is an exploded view of the first exemplified embodiment of the injection needle assembly of the present invention.
Figure 3:
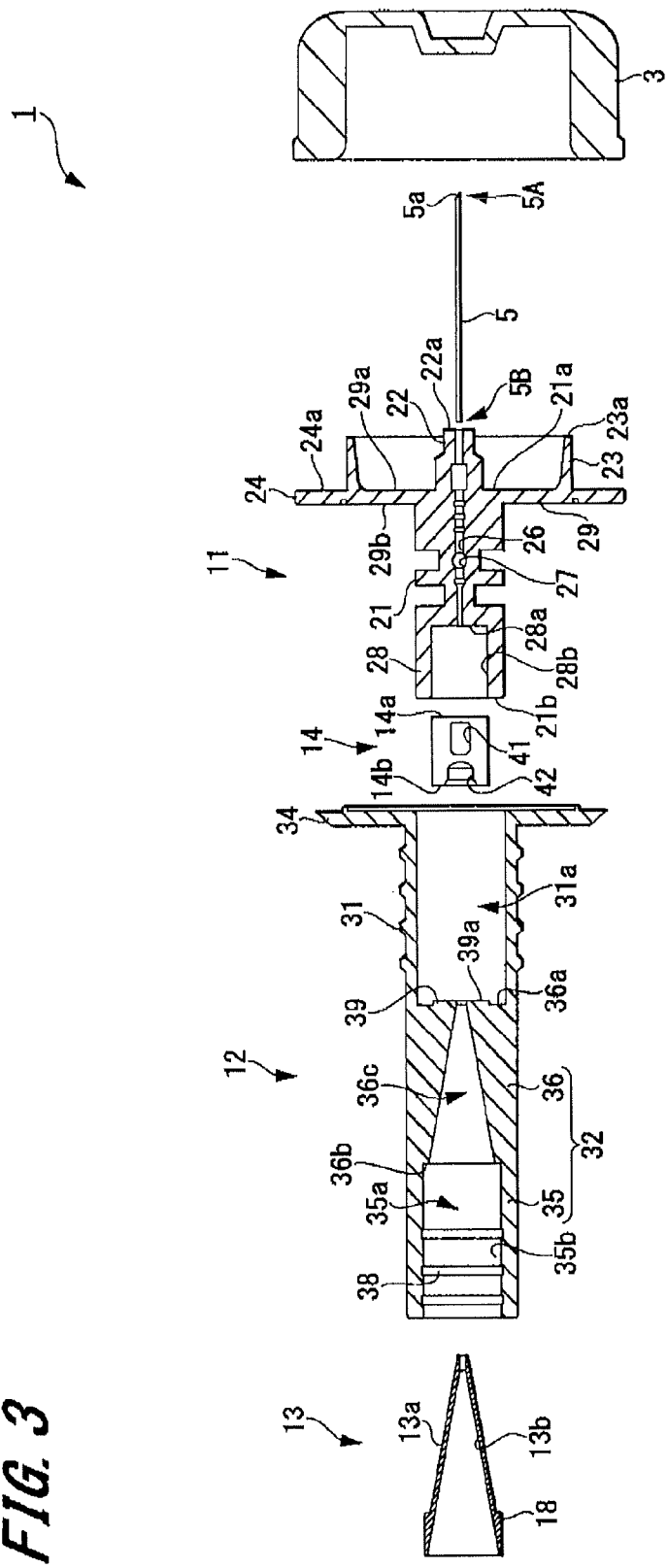
FIG. 3 is a cross-sectional view showing the first exemplified embodiment of the injection needle assembly of the present invention by being exploded.
Figure 4:
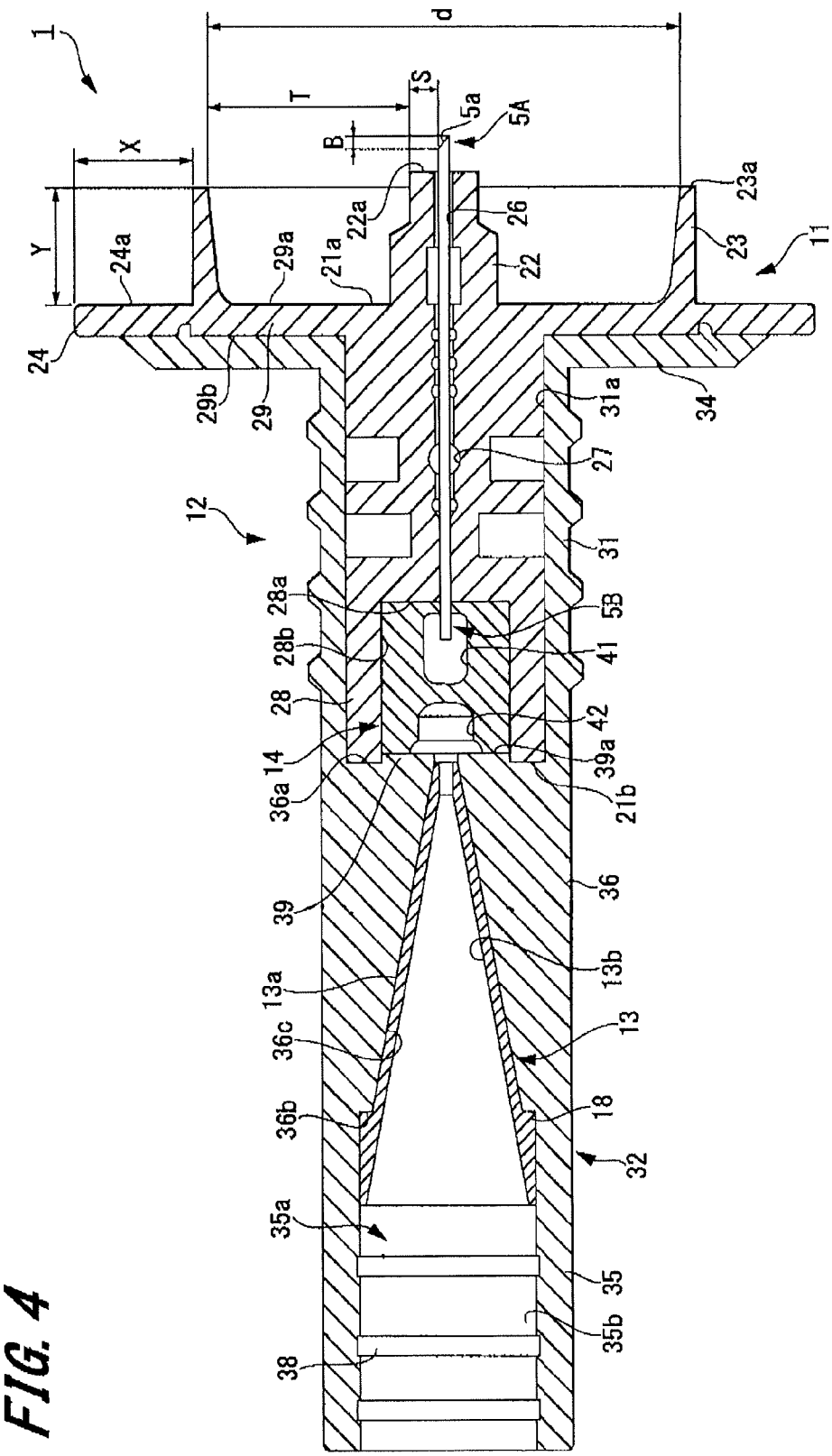
FIG. 4 is a cross-sectional view of the first exemplified embodiment of the injection needle assembly of the present invention.

FIG. 1 is a side view of a first exemplified embodiment of an injection needle assembly. FIG. 2 is an exploded view of the injection needle assembly. FIG. 3 is a cross-sectional view of a state in which the injection needle assembly is exploded. FIG. 4 is a cross-sectional view of the injection needle assembly.

An injection needle assembly 1 sticks a needle tip thereof from a skin surface and is used by being attached to an injector 52 (see FIG. 5) in case of injecting medicine into an upper layer region of the skin. It is possible for this injection needle assembly 1 to include a cap 3 attached detachably.

As shown in FIG. 2, the injection needle assembly 1 is composed of a hollow sticking needle tube 5 having a needle hole, a first member 11 for holding this sticking needle tube 5, a second member 12 connected to the first member 11 in a state of holding the sticking needle tube 5, a taper guide 13, and a connection portion 14.

For the sticking needle tube 5, there is used a tube having a size of 26 to 33 gauge (0.2 mm to 0.45 mm outer-diameter) according to the ISO standard of a needle tube for medication (ISO 9626:1991/Amd. 1:2001(E)) and preferably a tube having a size of 30 to 33 gauge.

One end of the sticking needle tube 5 is provided with a needle tip 5A having a bevel 5a. Hereafter, the other end of the sticking needle tube 5 lying on the opposite side of the needle tip 5A is referred to as the "proximal end 5B". It is enough if the length of the bevel 5a along the axial direction of the sticking needle tube 5 (hereinafter, the length is referred to as "bevel length B") is equal to or less than 1.4 mm, which is the minimum thickness of the skin upper layer region (for adults) to be described later and also, it is enough if the bevel length B is equal to or more than approximately 0.5 mm, which is a bevel length when a short bevel is formed on a 33 gauge needle tube. In other words, it is preferable for the bevel length B to be set in the range of 0.5 mm to 1.4 mm.

Further, it is more preferable for the bevel length B to be equal or less than 0.9 mm, which is the minimum thickness of the skin upper layer region (for infants), that is, it is more preferable for the bevel length B to be in the range of 0.5 mm to 0.9 mm. Note that the term "short bevel" means a bevel which is formed with an angle of 18° to 25° with respect to the longitudinal direction of the needle and which is generically used for injection needles.

For the material of the sticking needle tube 5, there can be cited, for example, stainless steel, but it is not limited by this material and it is possible to use aluminum, aluminum alloys, titanium, titanium alloys and other metals. Also, for the sticking needle tube 5, it is possible to use not only a straight needle but also a tapered needle which is tapered at least for a portion thereof. For the tapered needle, it is enough if there is employed a needle in which the proximal portion thereof has a larger diameter compared with that of the distal portion and a tapered structure is applied to an intermediate portion thereof. Also, the cross-sectional shape of the sticking needle tube 5 is not limited to a circle but may be a polygon such as a triangle.

Next, there will be explained the first member 11.

The first member 11 includes a needle holding portion 21, an adjustment portion 22, a stabilization portion 23, and a guide portion 24. As shown in FIG. 3, the needle holding portion 21 is formed approximately in a cylindrical shape and has end surfaces 21a and 21b perpendicular to the axial direction of the needle holding portion 21. The adjustment portion 22 is provided at a central portion of the end surface 21a of the needle holding portion 21 and is composed of a cylindrical projected portion projecting in the axial direction of the needle holding portion 21. The axis of this adjustment portion 22 coincides with the axis of the needle holding portion 21.

For the axis of the needle holding portion 21 and the adjustment portion 22, there is provided a through-hole 26 through which the sticking needle tube 5 passes. Then, for the needle holding portion 21, there is provided an injection hole 27 for injecting an adhesive agent (not shown) into the through-hole 26. This injection hole 27 opens on the outer peripheral surface of the needle holding portion 21 and communicates with the through-hole 26. More specifically, by virtue of the adhesive agent injected from the injection hole 27 into the through-hole 26, the sticking needle tube 5 is firmly attached fixedly to the needle holding portion 21.

The end portion on the end surface 21b side at the needle holding portion 21 is constituted to be a fitting portion 28 with which the connection portion 14 is fitted. This fitting portion 28 is a portion for showing one specific embodiment of a seal portion relating to the present invention. The fitting portion 28 is formed by providing an opened circular concave portion on the end surface 21b, and includes a bottom surface 28a in parallel with the end surfaces 21a, 21b and an inner circumferential surface 28b whose cross-section in parallel with the bottom surface 28a thereof becomes a circle. With respect to the bottom surface 28a of the fitting portion 28, a first abutting surface 14a mentioned later of the connection portion 14 will abut. Also, the outer circumferential surface of the connection portion 14 comes into close contact with the inner circumferential surface 28b of the fitting portion 28. With respect to this inner circumferential surface 28b, the luminal portion 41 mentioned later of the connection portion 14 is sealed in a liquid tight manner.

The outer peripheral surface of the needle holding portion 21 is provided with a connection piece 29. This connection piece 29 is formed as a ring-shaped flange projecting in the radial direction of the needle holding portion 21, and has flat surfaces 29a and 29b facing each other in the axial direction of the needle holding portion 21. The second member 12 is connected to the flat surface 29b of the connection piece 29. Also, the distal portion of the connection piece 29 constitutes a guide portion 24. This guide portion 24 will be described in detail later.

An end surface of the adjustment portion 22 constitutes a needle protrusion surface 22a from which the needle tip 5A side of the sticking needle tube 5 protrudes outward. The needle protrusion surface 22a is formed as a flat surface orthogonal to the axial direction of the sticking needle tube 5. When the sticking needle tube 5 is stuck into the skin upper layer region, this needle protrusion surface 22a contacts the surface of the skin and restricts the sticking depth. In other words, the depth to be stuck into the skin upper layer region by the sticking needle tube 5 is determined by the length of the sticking needle tube 5 protruding from the needle protrusion surface 22a (Hereinafter, this length will be referred to as "protrusion length L".) (see FIG. 4).

The thickness of the skin upper layer region is equivalent to the depth from the surface of the skin to the dermis layer and roughly, it is in the range of 0.5 mm to 3.0 mm. Therefore, it is possible for the protrusion length L of the sticking needle tube 5 to be set in the range of 0.5 mm to 3.0 mm.

Meanwhile, vaccines are generally administered into an upper arm region and in case of administration into a skin upper layer region, it is preferable to select a thick-skinned shoulder peripheral region, in particular, a deltoid region. In view of this, the thickness of the skin upper layer region at the deltoid muscle was measured with respect to 19 infants and 31 adults. This measurement was carried out by imaging the skin upper layer region having high ultrasonic reflectance by using an ultrasonic measuring apparatus (NP60R-UBM, a high-resolution echo system for small animals, produced by NEPA GENE CO., LTD.). Note that the measurement value showed log normal distribution and therefore, the range of MEAN±2SD was found according to the geometric mean.

As a result thereof, the thickness of the skin upper layer region at the deltoid muscles of infants was found to be 0.9 mm to 1.6 mm. Also, the thickness of the skin upper layer region at the deltoid muscles of adults was found to be 1.4 mm to 2.6 mm in a distal region, to be 1.4 mm to 2.5 mm in a central region and to be 1.5 mm to 2.5 mm in a proximal region. From the matters above, it was confirmed that the thickness of the skin upper layer region at the deltoid muscle is 0.9 mm or more for infants and 1.4 mm or more for adults. Therefore, in the injection into the skin upper layer region at the deltoid muscle, it is preferable for the protrusion length L of the sticking needle tube 5 to be set in the range of 0.9 mm to 1.4 mm.

By setting the protrusion length L in this manner, it is possible to reliably position the bevel 5a of the needle tip 5A in the skin upper layer region. As the result thereof, the needle hole (liquid medicine discharge port) opened at the bevel 5a can be located in the skin upper layer region regardless of the position thereof in the bevel 5a. Note that if the needle tip 5A is stuck into a position deeper than the skin upper layer region even in a case in which the liquid medicine discharge port is located in the skin upper layer region, the liquid medicine will flow into the subcutaneous region, so that the fact that the bevel 5a is reliably located within the skin upper layer region is important.

Note that in case of a needle tube thicker than 26 gauge, it is difficult to set the bevel length B to be 1.0 mm or less. Therefore, in order to set the protrusion length L of the sticking needle tube 5 to be within the preferable range (0.9 mm to 1.4 mm), it is preferable to use a needle tube thinner than 26 gauge.

The needle protrusion surface 22a is formed such that the distance S from its peripheral edge to the outer peripheral surface of the sticking needle tube 5 becomes 1.4 mm or less and is preferably formed within the range of 0.3 mm to 1.4 mm. This distance S from the outer peripheral edge of the needle protrusion surface 22a to the outer peripheral surface of the sticking needle tube 5 is set in consideration of the fact that a pressure is exerted on a water blister formed by injecting the medicine into the skin upper layer region. In other words, the needle protrusion surface 22a is set to be sufficiently smaller than the water blister to be formed in the skin upper layer region and to be a size which does not block the formation of the water blister. As a result thereof, even when the needle protrusion surface 22a presses the skin in the surroundings of the sticking needle tube 5, it is possible to prevent the injected medicine from leaking.

The stabilization portion 23 is formed in a cylindrical shape and protrudes from the flat surface 29a of the connection piece 29 provided on the needle holding portion 21. The sticking needle tube 5 and the adjustment portion 22 are disposed in a cylinder hole of the stabilization portion 23. In other words, the stabilization portion 23 is formed in a cylindrical shape and surrounds the adjustment portion 22 through which the sticking needle tube 5 passes and is provided by being apart from the needle tip 5A of the sticking needle tube 5 toward the radial direction.

The cap 3 is fitted detachably with the stabilization portion 23. This cap 3 covers the needle tip 5A of the sticking needle tube 5. For the materials of this cap 3, it is possible to cite synthetic resins such as polycarbonate, polypropylene, polyethylene and the like.

By attaching the cap 3 to the stabilization portion 23, it is possible to prevent the needle tip 5A from touching a user's finger or the like in case of attaching the injection needle assembly 1 to the injector 52 (see FIG. 5). Also, it is possible for the used injection needle assembly 1 or the medicine injection apparatus 51 mentioned later (see FIG. 5) to be constantly maintained in a safe condition and the user can carry out a disposal-treatment of the used injection needle assembly 1 or the medicine injection apparatus 51 operation without anxiety.

As shown in FIG. 3, the end surface 23a of the stabilization portion 23 is located on the side of the proximal end 5B of the sticking needle tube 5 compared with the needle protrusion surface 22a of the adjustment portion 22. When the needle tip 5A of the sticking needle tube 5 is stuck into a living body, the needle protrusion surface 22a first comes into contact with the surface of the skin and thereafter, the surface of the skin touches the end surface 23a of the stabilization portion 23. At that time, by the fact that the end surface 23a of the stabilization portion 23 contacts with the skin, the medicine injection apparatus 51 (see FIG. 5) is stabilized and it is possible to keep the sticking needle tube 5 in a posture of being approximately perpendicular to the skin.

Note that even if the end surface 23a of the stabilization portion 23 is made to locate on the same plane as the needle protrusion surface 22a and also, even if it is made to locate on the side of the needle tip 5A of the sticking needle tube 5 compared with the needle protrusion surface 22a, it is possible to maintain the sticking needle tube 5 in a posture approximately perpendicular to the skin. Also, when taking the bulging of the skin into account on an occasion of pressing the stabilization portion 23 against the skin, it is preferable for the distance between the end surface 23a of the stabilization portion 23 and the needle protrusion surface 22a along the axial direction to be set to 1.3 mm or less.

The inner diameter d of the stabilization portion 23 is set to be equal to or greater than the diameter of the water blister which is formed on the skin. Specifically, the distance T from the inner wall surface of the stabilization portion 23 to the outer peripheral edge of the needle protrusion surface 22a is set so as to fall into a range of 4 mm to 15 mm. Thus, a pressure is never exerted on the water blister from the inner wall surface of the stabilization portion 23 and it is possible to prevent the water blister formation from being disturbed.

If the distance T from the inner wall surface of the stabilization portion 23 to the peripheral edge of the needle protrusion surface 22a is selected to be 4 mm or more, there is no upper limit for the distance thereof. However, when the distance T is increased, the outside diameter of the stabilization portion 23 becomes larger, so that in case of sticking the sticking needle tube 5 into a slender arm such as the arm of an infant, it becomes difficult to bring the whole portion of the end surface 23a of the stabilization portion 23 into contact with the skin. Therefore, taking the slenderness of an infant's arm into account, it is preferable to define the distance T to be 15 mm for the maximum value.

Provided that the distance S from the peripheral edge of the needle protrusion surface 22a to the outer peripheral surface of the sticking needle tube 5 is 0.3 mm or more, the adjustment portion 22 does not enter into the skin. Therefore, taking into account the distance T (4 mm or more) from the inner wall surface of the stabilization portion 23 to the peripheral edge of the needle protrusion surface 22a and the diameter (approximately 0.3 mm) of the needle protrusion surface 22a, it is possible to set the inner diameter d of the stabilization portion 23 to be 9 mm or more.

Note that the shape of the stabilization portion 23 is not limited to a cylindrical shape and it is allowed, for example, to form the shape as an angled tubular shape such as a quadratic prism, a hexagonal prism or the like having a tubular hole in the center thereof.

The guide portion 24 is that portion of the connection piece 29 which is located on the distal side compared with the stabilization portion 23. This guide portion 24 has a contact surface 24a to be brought into contact with the skin. The contact surface 24a is a portion of the flat surface 29a of the connection piece 29 and is a flat surface approximately in parallel with the end surface 23a of the stabilization portion 23. By pressing the stabilization portion 23 toward the skin until the contact surface 24a of the guide portion 24 makes contact with the skin, it is possible to secure a force with which the stabilization portion 23 and the sticking needle tube 5 are pressed toward the skin in a range of a predetermined value or more. Thus, the portion of the sticking needle tube 5 which protrudes from the needle protrusion surface 22a (portion corresponding to protrusion length L) will be stuck into the skin reliably.

The distance (This will hereinafter be referred to as "guide-portion height".) Y from the contact surface 24a of the guide portion 24 to the end surface 23a of the stabilization portion 23 is set such that the sticking needle tube 5 and the stabilization portion 23 can be pressed toward the skin and stick it with an appropriate pressure. Thus, the pressure exerted on the skin by the sticking needle tube 5 and the stabilization portion 23 is guided by the guide portion 24, in which it is possible to reliably locate the needle tip 5A (the bevel 5a) of the sticking needle tube 5 in the skin upper layer region and concurrently, it is possible for the user to get a feeling of security. Note that the appropriate pressing force with which the sticking needle tube 5 and the stabilization portion 23 are pressed toward the skin is, for example, 3 to 20 N.

In a case in which the inner diameter d of the stabilization portion 36 is in the range of 11 mm to 14 mm, the guide-portion height Y is appropriately determined based on the length (This will hereinafter be referred to as "guide-portion length".) X from the distal end surface of the guide portion 37 to the outer peripheral surface of the stabilization portion 36. For example, when the inner diameter d of the stabilization portion 23 is 12 mm and the guide-portion length X is 3.0 mm, the guide-portion height Y is set in the range of 2.3 mm to 6.6 mm.

Next, there will be explained the second member 12.

The second member 12 is formed to be approximately a cylindrical shape. One end portion in the axial direction of this second member 12 is formed to be an insertion portion 31 into which the needle holding portion 21 of the first member 11 is inserted and the other end portion is formed to be an engagement portion 32 with which an injection barrel 54 (see FIG. 5) mentioned later of the injector 52 engages.

The tube hole 31a (see FIG. 3) of the insertion portion 31 is set to have a size corresponding to the needle holding portion 21 of the first member 11. At the outer circumferential surface of this insertion portion 31, there is provided a fixing piece 34 which is connected to the connection piece 29 of the first member 11. This fixing piece 34 is formed as a ring-shaped flange projecting to the radially outward direction of the insertion portion 31. The flat surface 29b of the connection piece 29 provided on the first member 11 abuts on and is firmly fixed to the fixing piece 34. For the fixing method between the fixing piece 34 and the connection piece 29, there can be cited methods using an adhesive agent, ultrasonic fusing, laser fusing, fixation screws and the like.

The engagement portion 32 is composed of a fit tube 35 into which the injection barrel 54 (see FIG. 5) of the injector 52 is to be fitted and a guide fixing portion 36 at which the taper guide 13 is arranged. The fit tube 35 is formed in a cylindrical shape having a circular tube hole 35a. On the inner circumferential surface 35b of the fit tube 35 which forms the tube hole 35a, there are formed a plurality of elongated protrusion portions 38 which protrude continuously to a circumferential direction. This elongated protrusion portion 38 abuts the outer circumferential surface of the injection barrel 54.

The guide fixing portion 36 is provided between the fit tube 35 and the insertion portion 31. This guide fixing portion 36 is formed approximately in a cylindrical shape and includes an end surface 36a continuous to the insertion portion 31, an end surface 36b continuous to the fit tube 35, a communicating hole 36c which communicates between the tube hole 35a of the fit tube 35 and the tube hole 31a of the insertion portion 31.

On the end surface 36a of the guide fixing portion 36, there is provided a protrusion portion 39 which protrudes inside the tube hole 31a of the insertion portion 31. This protrusion portion 39 is formed in a ring shape protruding approximately vertically from the end surface 36a and concurrently acts as an opening portion of the communicating hole 36c. Then, at the protrusion portion 39, there is provided a pressing surface 39a which presses a second abutting surface 14b mentioned later of the connection portion 14. The pressing surface 39a of the protrusion portion 39 is set to be a size approximately equal to the second abutting surface 14h of the connection portion 14 and surface-contacts the second abutting surface 14b.

The communicating hole 36c is formed approximately in a conical shape and the diameter thereof becomes continuously smaller toward the tube hole 31a of the insertion portion 31. As shown in FIG. 4, at the communicating hole 36c, there is arranged a taper guide 13.

Note that for the materials of the first member 11 and the second member 12 which are mentioned above, there can be cited synthetic resins (plastics) such as polycarbonate, polypropylene, polyethylene and the like.

Next, there will be explained the taper guide 13.

The taper guide 13 is formed approximately in a conical tubular shape by a material having hardness equivalent to or higher than that of the needle tube 53 made of SUS304, titanium, ceramic or the like. On the outer surface 13a of this taper guide 13, there is provided a guide stage portion 18 which abuts the end surface 36b of the fixing portion 36. Owing to the fact that this stage portion 18 abuts the end surface 36b of the guide fixing portion 36, the taper guide 13 is positioned with respect to the guide fixing portion 36.

Between the inner surface of the guide fixing portion 36 which forms the communicating hole 36c and the outer surface 13a of the taper guide 13, an adhesive agent (not shown) is applied. By this adhesive agent, the taper guide 13 is firmly fixed to the guide fixing portion 36.

The inner surface 13b of the taper guide 13 forms a circular tube hole and the diameter thereof continuously becomes smaller as it leads from the end portion on the fit tube 35 side toward the end portion on the insertion portion 31 side. The inner surface 13b of this taper guide 13 guides the movement of the needle tube 53 of the injector 52 such that the needle tube 53 heads toward the after-mentioned luminal portion 41 at the connection portion 14.

Next, there will be explained the connection portion 14. The connection portion 14 is formed by a material selected from various kinds of rubber materials such as natural rubber, silicone rubber and the like, various thermoplastic elastomers based on polyurethane, styrene and the like, and elastic materials formed by mixtures of the above materials.

The connection portion 14 is formed in a cylindrical shape and includes the first abutting surface 14a and the second abutting surface 14b, which are perpendicular to the axial direction. The length in the axial direction of this connection portion 14 is set to be approximately equal to the length in the axial direction of the fitting portion 28 provided at the needle holding portion 21. The first abutting surface 14a of the connection portion 14 abuts the bottom surface 28a of the fitting portion 28 provided at the needle holding portion 21, and the second abutting surface 14b abuts the pressing surface 39a of the protrusion portion 39 provided at the engagement portion 32.

At the connection portion 14, there is provided the luminal portion 41 which is opened on the outer circumferential surface. The connection portion 14 defines a first cross sectional area and the luminal portion 41 defines a second cross sectional area, the second cross sectional area being less than the first cross sectional area. When the connection portion 14 is fitted into the fitting portion of the needle holding portion 21, the luminal portion 41 is sealed in a liquid tight manner by the fitting portion 28 provided at the needle holding portion 21. It is possible to mold the connection portion 14 including a luminal portion (space) sealed in a liquid tight manner if a split mold is used, but the molding cost thereof increases. Therefore, in this exemplified embodiment, the luminal portion 41 is opened on the outer circumferential surface of the connection portion 14 and by closing the opening thereof by means of the fitting portion 28, the molding of the connection portion 14 is made easy.

As shown in FIG. 4, the proximal end 5B of the sticking needle tube 5 is inserted into the connection portion 14 from the first abutting surface 14a and is arranged at the luminal portion 41. Then, when the injection needle assembly 1 is attached to the injector 52 (see FIG. 5), the ejection port in the needle tube 53 of the injector 52 is inserted into the connection portion 14 from the second abutting surface 14b and is arranged at the luminal portion 41. In other words, the connection portion 14 creates liquid-tight communication between the sticking needle tube 5 of the injection needle assembly 1 and the needle tube 53 of the injector 52.

Also, at the second abutting surface 14b of the connection portion 14, there is provided a deformation assistance concave portion 42. By providing this deformation assistance concave portion 42, when the connection portion 14 is pressed by the pressing surface 39a of the engagement portion 32, the connection portion 14 deforms elastically so as to expand toward the outside (inner circumferential surface 28b side of fitting portion 28). As a result thereof, it is possible to bring the outer circumferential surface of the connection portion 14 and the inner circumferential surface of the fitting portion 28 into close contact reliably and it is possible to seal the luminal portion 41 in a liquid tight manner.

Also, in a state in which the injection needle assembly 1 has been assembled, the protrusion portion 39 of the second member 12 is inserted into the fitting portion 28 of the first member 11. Thus, it is possible to press the connection portion 14 reliably and to deform it elastically.

[Medicine Injection Apparatus]

Next, there will be explained a second exemplified embodiment of the medicine injection apparatus of the present invention with reference to FIG. 5.

FIG. 5A is a side view of a state immediately before assembling the medicine injection apparatus. FIG. 5B is a cross-sectional view of a state in which the medicine injection apparatus has been assembled.

The medicine injection apparatus 51 is constituted by an injector 52 and injection needle assembly 1 attached to this injector 52 (see FIG. 5B). The injector 52 is provided with a hollow needle tube 53 and an injection barrel 54 mounted with this needle tube 53.

As shown in FIG. 5A, at one end of the needle tube 53, there is provided a needle tip 53A having a bevel 53a. For the material of this needle tube 53, there can be cited, for example, stainless steel, but it is not limited by this and it is possible to use aluminum, aluminum alloys, titanium, titanium alloys and other metals. Also, for the needle tube 53, it is possible to use not only a straight needle but also a tapered needle, at least whose portion is in a tapered form. As for the tapered needle, it is enough if there is employed a needle in which the proximal portion thereof has a large diameter compared with that of the distal portion and a tapered structure is applied to an intermediate portion therebetween. Also, the cross-sectional shape of the needle tube 53 is not limited to a circle but may be a polygon such as a triangle.

The injection barrel 54 is provided with a tube main body 55 and a needle hub 56 continuous to the distal end of this tube main body 55. The tube main body 55 is composed of a circular tube body. The needle hub 56 is composed of a circular tube body having an outer diameter smaller than that of the tube main body 55. This needle hub 56 is fitted into the engagement portion 32 of the injection needle assembly 1 detachably.

In the inside of the needle hub 56, there is provided a needle insertion portion 56a into which the proximal side of the needle tube 53 is inserted. The needle tube 53 inserted into this needle insertion portion 56a communicates with the inside of the tube main body 55. The needle tube 53 is fixed on the needle hub 56 firmly by an adhesive agent (not shown) injected into the needle insertion portion 56a.

Note that the needle hub 56 of this exemplified embodiment is formed so as not to create space between the needle tube 53 and the tube main body 55, whereby it is difficult for the medicine to remain in the injection barrel 54. Thus, it is possible not to detract from the merit of reducing the quantity of antigen, which is obtained by administering the vaccine into the skin upper layer region.

A gasket 57 is housed in the tube main body 55. The space inside the tube main body 55 is partitioned in a liquid-tight manner by the gasket 57 and one space which communicates with the needle tube 53 forms a liquid chamber 60. In the other space in the tube main body 55, there is disposed a plunger 58. One end (distal end) of this plunger 58 is connected to the gasket 57 and the other end (proximal end) of the plunger 58 protrudes from an opening (not shown) of the tube main body 55. By operating this plunger 58, the gasket 57 is moved in the axial direction inside the tube main body 55, whereby suction of a medicine into the liquid chamber 60 and discharge of the medicine filling the liquid chamber 60 are carried out.

As the material of the injection barrel 54, it is possible to use a synthetic resin such as polycarbonate, polypropylene, polyethylene or the like and besides, it is also allowed to use glass or the like.

[Assembling Method for Medicine Injection Apparatus]

Next, there will be explained an assembling method of the medicine injection apparatus 51.

The medicine injection apparatus 51 is assembled by mounting the injection needle assembly 1 to the injector 52. In order to mount the injection needle assembly 1 to the injector 52, the needle tube 53 is inserted from the engagement portion 32 side of the injection needle assembly 1 and the needle hub 56 is fitted into the fit tube 35 of the engagement portion 32. Thus, the mounting of the medicine injection apparatus 51 is completed. The fit-in operation of the needle hub 56 is stopped by a mechanism that the end surface of the engagement portion 32 abuts the tube main body 55.

The needle tube 53 inserted from the engagement portion 32 side progresses inside the taper guide 13 after passing through the engagement portion 32. At that time, if the needle tube 53 does not progress toward the luminal portion 41 of the connection portion 14, it is possible for the needle tube 53 to be guided by the inner surface 13b of the taper guide 13 and to move toward the luminal portion 41 of the connection portion 14. Thereafter, the needle tip 53A of the needle tube 53 is inserted into the connection portion 14 from the second abutting surface 14b and is arranged at the luminal portion 41. Therefore, it is possible to arrange the needle tip 53A at the luminal portion 41 easily. When the needle tip 53A is arranged at the luminal portion 41, the needle tube 53 and the sticking needle tube 5 of the injection needle assembly 1 communicate with each other in a liquid tight manner through the luminal portion 41.

Also, the stabilization portion 23 of the injection needle assembly 1 is equipped with the cap 3. Therefore, when the injection needle assembly 1 is attached to the injector 52, the needle tip 5A of the sticking needle tube 5, which protrudes from the needle protrusion surface 22a, can be prevented from touching the user's fingertips or the like. Note that, when the needle tip 5A of the sticking needle tube 5 is stuck into the skin upper layer region by using the medicine injection apparatus 51, the cap 3 is removed from the stabilization portion 23.

In the injection needle assembly 1 of this exemplified embodiment, the proximal end 53 of the sticking needle tube 5 held by the needle holding portion 21 is arranged at the luminal portion 41 of the connection portion 14. Therefore, by inserting the needle tube 53 of the injector 52 into the connection portion 14, it is possible to communicate the needle tube 53 and the sticking needle tube 5 in a liquid tight manner through the luminal portion 41.

Also, according to the injection needle assembly 1 of this exemplified embodiment, since the movement of the needle tube 53 is guided by the taper guide 13, it is possible to decide the insertion position of the needle tube 53 at the second abutting surface 14b of the connection portion 14 highly accurately. As a result thereof, it is possible to make the luminal portion 41 small and to reduce the amount of medicine remaining in the luminal portion 41.

[Use Method of Medicine Injection Apparatus]

Next, there will be explained a method of using the disclosed medicine injection apparatus 51.

In order to stick the needle tip 5A of the sticking needle tube 5 into the skin upper layer region, first, the end surface 36a of the stabilization portion 36 is made to face the skin. Thus, the needle tip 5A of the sticking needle tube 5 is made to face the skin into which it is to be stuck. Next, the medicine injection apparatus 51 is moved approximately perpendicularly with respect to the skin, the needle tip 5A is stuck into the skin and concurrently, the end surface 23a of the stabilization portion 23 is pressed against the skin. At that time, the needle protrusion surface 22a contacts the skin. Therefore, it is possible to deform the skin flatly and it is possible to stick the needle tip 5A side of the sticking needle tube 5 into the skin by as much as the protrusion length L.

Next, the end surface 23a of the stabilization portion 23 is pressed until the contact surface 24a of the guide portion 24 comes into contact with the skin. Here, regarding the guide-portion height Y, this length is set such that it is possible for the sticking needle tube 5 and the stabilization portion 23 to be stuck into the skin with a proper pressure. Therefore, the pressure which presses the skin becomes a predetermined value by the stabilization portion 23.

As a result thereof, it is possible to make the user recognize the proper pressure for the stabilization portion 23, and it is possible to locate the needle tip 5A and the bevel 5a of the sticking needle tube 5 reliably in the skin upper layer region. In this manner, depending on the fact that the guide portion 24 becomes a mark for recognizing the proper pressure for the stabilization portion 23, it is possible for the user to use the medicine injection apparatus 51 without anxiety.

Also, by a mechanism that the end surface 23a of the stabilization portion 23 abuts the skin, the posture of the medicine injection apparatus 51 is stabilized and it is possible to stick the sticking needle tube 5 with respect to the skin in a straight manner. Furthermore, it is possible to prevent a shaking of the sticking needle tube 5, which occurs after the sticking, so that it is possible to carry out stable administration of the medicine.

In case of an extremely small protrusion length L of, for example, approximately 0.5 mm, there may be a case in which the needle tip 5A is not stuck into the skin even if the needle tip is brought into abutment with the skin. However, caused by a mechanism in which the skin pressed against the stabilization portion 23 is pressed down perpendicularly, the skin on the inner side of the stabilization portion 23 is pulled and there is created a state in which tension is applied to the skin. Therefore, it becomes difficult for the skin to escape with respect to the needle tip 5A of the sticking needle tube 5. Accordingly, by providing the stabilization portion 23, there can be also obtained such an effect that the needle tip 5A is stuck into the skin more easily.

After sticking the needle point 5A of the sticking needle tube 5 into the skin, the plunger 58 is pushed and the gasket 57 is moved toward the needle hub 56 side. Thus, the medicine filling the liquid chamber 60 of the tube main body 55 is pushed out from the liquid chamber 60 and is ejected from the needle tip 53A (ejection port) of the needle tube 53. Then, the medicine ejected from the needle tip 53A enters the sticking needle tube 5 through the luminal portion 41 and is injected into the skin upper layer region from the needle tip 5A.

2. Second Exemplified Embodiment

Injection Needle Assembly

Next, there will be explained a second exemplified embodiment of the injection needle assembly of the present invention with reference to FIG. 6.

Figure 6:
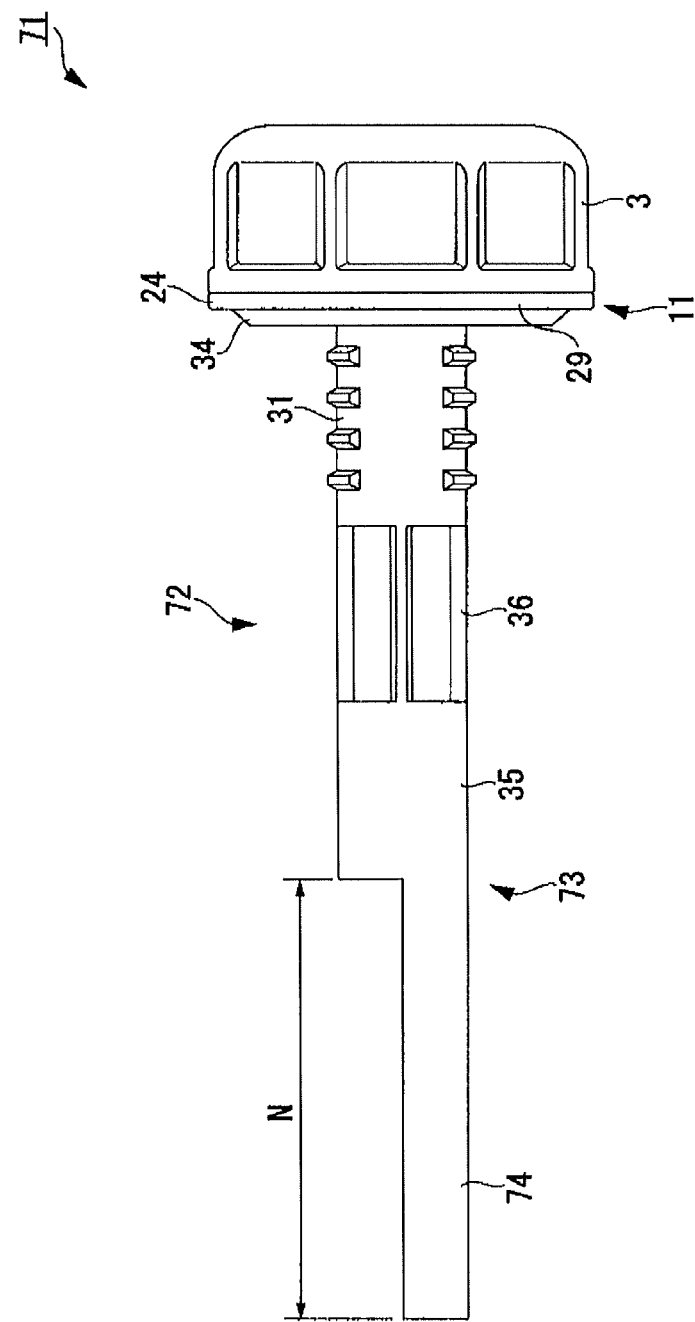
FIG. 6 is a side view of a second exemplified embodiment of an injection needle assembly of the present invention.

FIG. 6 is a cross-sectional view of a second exemplified embodiment of the injection needle assembly.

As shown in FIG. 6, an injection needle assembly 71 includes constitutions similar to those of the injection needle assembly 1 of the first exemplified embodiment. An aspect in which this injection needle assembly 71 is different from the injection needle assembly 1 is that an attachment guide portion 74 is provided at the second member 72. Therefore, there will be explained the attachment guide portion 74 here, and repetitive explanation will be omitted by applying the same reference numerals to the portions in common with those of the injection needle assembly 1.

The second member 72 of the injection needle assembly 71 is provided with the insertion portion 31 and an engagement portion 73. Then, the engagement portion 73 is constituted by the fit tube 35, the guide fixing portion 36 and the attachment guide portion 74. The attachment guide portion 74 is provided so as to be continuous to the end surface of the fit tube 35. This attachment guide portion 74 is formed in an arc shape having a center angle of 180 degrees, in other words, in a halved cylindrical shape.

The outer circumferential surface of tube main body 55 of the injector 52 abuts an inner surface 74a of the attachment guide portion 74 (see FIG. 7) in a slidable manner. There is a configuration in which when the outer circumferential surface of the tube main body 55 abuts the inner surface 74a of the attachment guide portion 74, the axial center of the needle tube 53 moves toward the luminal portion 41 of the connection portion 14.

Also, the distance N from the distal end of the attachment guide portion 74 to the end surface of the fit tube 35 is set to be longer than the distance M (see FIG. 7) from the end surface, at which the needle hub 56 of the tube main body 55 protrudes, to the needle tip 53A of the needle tube 53. Therefore, by moving the injector 52 toward a direction intersecting the axial direction, it is possible to make the outer circumferential surface of the tube main body 55 abut onto the inner surface 74a of the attachment guide portion 74.

In this exemplified embodiment, the attachment guide portion 74 is formed in an arc shape having a center angle of 180 degrees, but it is allowed for the center angle of the attachment guide relating to the present invention to be smaller than 180 degrees. Also, as for the shape of the attachment guide relating to the present invention, it is not to be limited by the arc shape and, for example, three side plates, each of which linearly contacts the outer circumferential surface of the tube main body 55, are allowed to be constituted in a continuous manner such that the cross-section thereof becomes an approximate C-shape.

[Assembling Method of Medicine Injection Apparatus]

Next, there will be explained an assembling method of a medicine injection apparatus 81 with reference to FIG. 7.

Figure 7A:
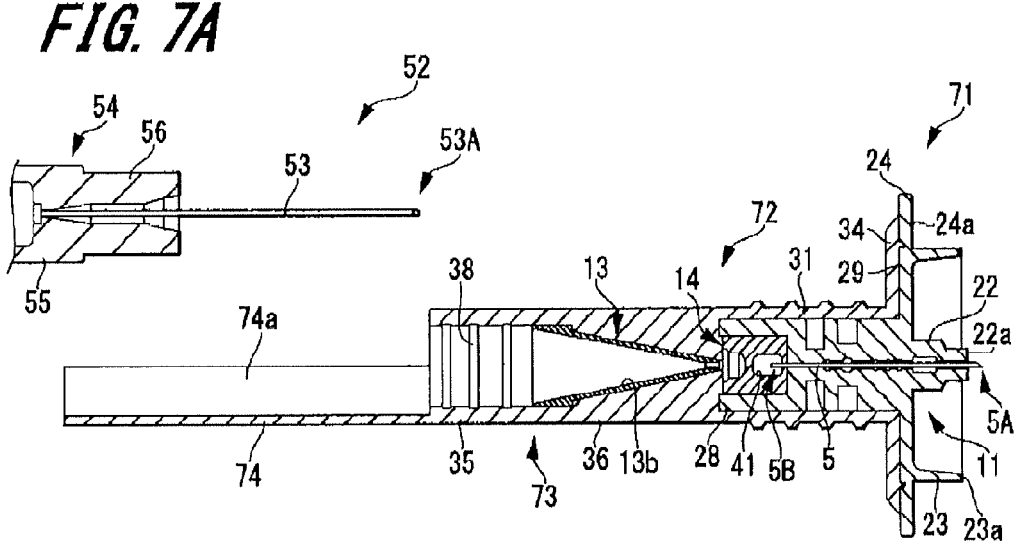
FIG. 7A is an explanatory view of a state in which the injector is moved toward a direction intersecting the axial direction and is made to approach the injection needle assembly of the second exemplified embodiment.
Figure 7B:
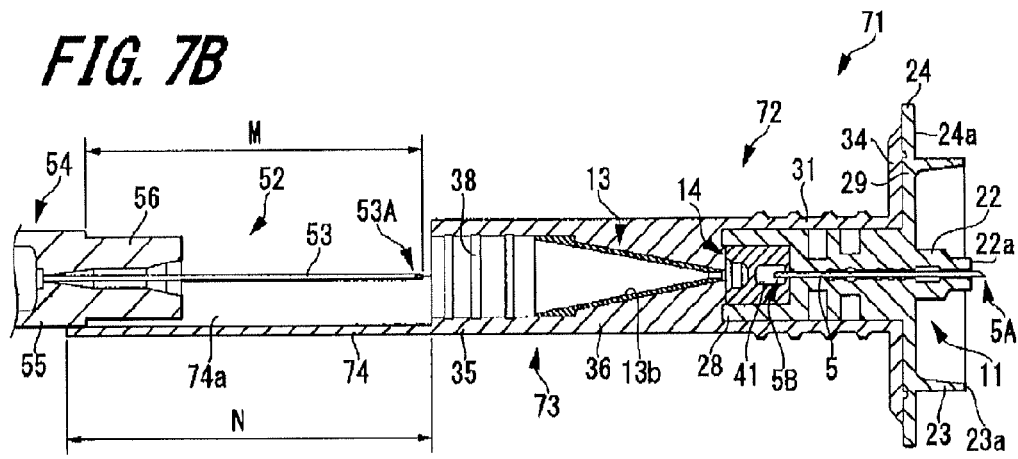
FIG. 7B is an explanatory view of a state in which an injection barrel of the injector abuts an attachment guide portion relating to the injection needle assembly of the second exemplified embodiment.
Figure 7C:
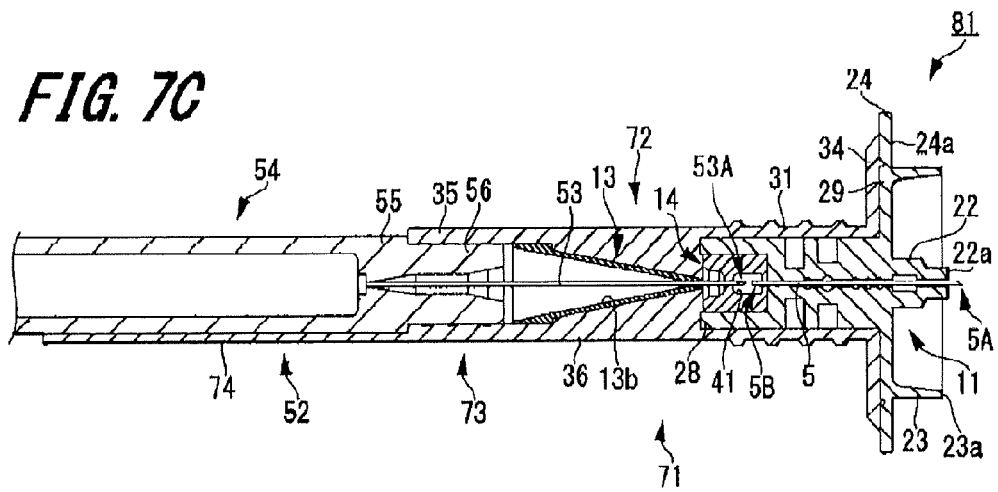
FIG. 7C is an explanatory view of a state in which the injection needle assembly of the second exemplified embodiment is attached to the injector.

FIG. 7A is an explanatory view of a state in which the injector 52 is moved to a direction intersecting the axial direction and is made to approach the injection needle assembly 71. FIG. 7B is an explanatory view of a state in which the tube main body 55 of the injector 52 abuts the inner surface 74a of the attachment guide portion 74 in the injection needle assembly 71. FIG. 7C is an explanatory view of a state in which the attachment of the injection needle assembly 71 with respect to the injector 52 has been completed.

The medicine injection apparatus 81 is assembled by attaching the injection needle assembly 71 to the injector 52. In order to attach the injection needle assembly 71 to the injector 52, first, the injector 52 is moved in a direction intersecting the axial direction of the needle tube 53 and made to approach the attachment guide portion 74 of the injection needle assembly 71 (see FIG. 7A).

Subsequently, the outer circumferential surface of the tube main body 55 of the injector 52 is made to abut the inner surface 74a of the attachment guide portion 74 (see FIG. 7B). Thus, it is possible to easily carry out the positioning of the needle tube 53 in a direction intersecting the axial direction. As a result thereof, the needle tip 53A of the needle tube 53 faces the fit tube 35 of the engagement portion 73. Also, the attachment guide portion 74 is formed in an arc shape whose center angle is approximately 180 degrees, so that it is possible for the injector 52 not to deviate in a direction intersecting the axial direction.

Next, the injector 52 is moved in the axial direction, the needle hub 56 of the injector 52 is fitted into the fit tube 35, and the assembly of the medicine injection apparatus 81 is completed (see FIG. 7C). The fit-in operation of this needle hub 56 is stopped by a mechanism that the end surface of the fit tube 35 abuts the tube main body 55. At that time, by moving the injector 52 along the inner surface 74a of the attachment guide portion 74, it is possible to fit the needle hub 56 into the fit tube 35 easily.

Also, even if bend deformation occurs at the needle tube 53 when the needle tube 53 is passed through the rubber stopper of the vial, the needle tube 53 is guided to the inner surface 13b of the taper guide 13, so that it proceeds toward the luminal portion 41. Therefore, it is possible to arrange the needle tip 53A of the needle tube 53 at the luminal portion 41 reliably. Then, it is possible to communicate the needle tube 53 of the injector 52 and the sticking needle tube 5 of the injection needle assembly 71 in a liquid tight manner through the luminal portion 41.

Also, in the medicine injection apparatus 81, there is exposed a half of the tube main body 55 in the circumferential direction within the outer circumferential surface thereof, so that it is possible to visibly confirm the scale provided at the tube main body 55 of the injector 52.

As described above, there were explained exemplified embodiment of the injection needle assembly and the medicine injection apparatus of the present invention together with the operational effects thereof. However, the injection needle assembly and the medicine injection apparatus of the present invention are not to be limited by the exemplified embodiments mentioned above and it is possible to employ various kinds of modified practices within the scope without departing from the gist of the invention described in the claims.

In the exemplified embodiment mentioned above, the fit tube 35 having a tubular shape is provided at the engagement portion 32 (73) and it is constituted such that the needle hub 56 of the injector 52 is fitted into the fit tube 35. However, as for the engagement portion relating to the present invention, it is not to be limited by the tubular shape and it is possible to employ an appropriate change according to the shape and the constitution of the injection barrel to be attached. For example, it is also possible to employ a constitution in which the engagement portion is screwed to the injection barrel.

Also, in the exemplified embodiment mentioned above, the taper guide 13 was formed approximately in a conical tubular shape. However, for the taper guide relating to the present invention, it is enough if the guide has an inner surface whose diameter becomes continuously smaller toward the connection portion, and it is possible for its outward appearance to be formed appropriately according to the shape of the guide fixing portion.

Also, in the exemplified embodiment mentioned above, the stabilization portion 23 and the guide portion 24 were provided at the first member 11 (needle holding portion). However, it is also possible for the stabilization portion and the guide portion relating to the present invention to be provided at the second member (engagement portion) or at the injector.

Also, in the exemplified embodiment mentioned above, at the first member 11 (needle holding portion 21), there was provided the seal portion (fitting portion 28) for sealing the luminal portion 41 of the connection portion 14. However, the seal portion relating to the present invention is allowed to be provided at the second member 12 (engagement portion). Also, the seal portion relating to the present invention is not limited by a portion fitted to the connection portion and it is enough if the seal portion is a portion by which the opening of the luminal portion is sealed in a liquid tight manner.

Also, in the exemplified embodiment mentioned above, there was employed a constitution in which the needle holding portion 21 and the engagement portion 32 (73) are formed separately as individual bodies and thereafter, they are connected. However, it is also possible for the needle holding portion and the engagement portion relating to the present invention to be formed integrally.

DESCRIPTION OF REFERENCE NUMERALS 1, 71: injection needle assembly; 3: cap; 5: sticking needle tube; 5A: needle tip; 5a: bevel; 5B: proximal end; 11: first member; 12, 72: second member; 13: taper guide; 13a: outer surface; 13b: inner surface; 14: connection portion; 14a: first abutting surface; 14b: second abutting surface; 21: needle holding portion; 22: adjustment portion; 22a: needle protrusion surface; 23: stabilization portion; 23a: end surface; 24: guide portion; 24a: contact surface; 28: fitting portion (seal portion); 28a: bottom surface; 28b: inner circumferential surface; 31: insertion portion; 32, 73: engagement portion; 35: fit tube; 36: guide fixing portion; 39: protrusion portion; 39a: pressing surface; 41: luminal portion; 42: deformation assistance concave portion; 51, 81: medicine injection apparatus; 52: injector; 53: needle tube; 53A: needle tip (ejection port); 54: injection barrel; 55: tube main body; 56: needle hub; 57: gasket; 58: plunger; 60: liquid chamber; 74: attachment guide portion; 74a: inner surface

The invention claimed is:

1. An injection needle assembly used by being attached to an injector including an injection barrel filled with medicine and an injector needle tube, comprising:

a sticking needle tube having a needle tip to be stuck into a skin;

a needle holding portion for holding the sticking needle tube;

an engagement portion engaged with the injection barrel; and a connection portion which includes a luminal portion and the connection portion includes a first abutting surface abutting the needle holding portion and a second abutting surface abutting the engagement portion;

wherein a proximal end of the sticking needle tube, opposite to the needle tip of the sticking needle tube, is arranged in said luminal portion, an ejection port of the injector needle tube of the injector is arranged in said luminal portion, and said luminal portion of the connection portion thereby connects the sticking needle tube and the injector needle tube with each other in fluid communication in a liquid tight manner.

2. The injection needle assembly according to claim 1, wherein the proximal end of the sticking needle tube is inserted from the first abutting surface into the luminal portion, and the ejection port in the injector needle tube of the injector is inserted from the second abutting surface into the luminal portion.

3. The injection needle assembly according to claim 2, wherein the connection portion includes the first abutting surface and the second abutting surface which face each other, and an outer circumferential surface which is continuous to the first abutting surface and the second abutting surface and also in which the luminal portion is opened; and the needle holding portion or the engagement portion includes a seal portion for sealing the luminal portion in a liquid tight manner by closely contacting with the outer circumferential surface of the connection portion.

4. The injection needle assembly according to claim 1, comprising an adjustment portion which is provided at the periphery of the sticking needle tube and on which there is formed a needle protrusion surface which abuts the skin when sticking the sticking needle tube into a living body and thereby restricts a sticking depth of the sticking needle tube.

5. The injection needle assembly according to claim 4, wherein the sticking needle tube is projected from the needle protrusion surface by the range of 0.5 mm to 3.0 mm.

6. The injection needle assembly according to claim 1, wherein at the needle holding portion or the engagement portion, there is formed a stabilization portion which is arranged apart from the needle tip of the sticking needle tube in the radius direction and which contacts with the skin when sticking the needle tip of the sticking needle tube into the living body and thereby maintains the sticking needle tube in an approximately perpendicular posture to the skin.

7. The injection needle assembly according to claim 1, comprising an attachment guide portion which is provided continuously to the engagement portion and carries out positioning of the injector such that the ejection port of the injector needle tube faces the luminal portion of the connection portion by a mechanism in which the engagement portion abuts the injection barrel before engaging with the injection barrel.

8. The injection needle assembly according to claim 1, comprising a taper guide which is arranged at the engagement portion and which has an inner surface whose diameter becomes continuously smaller toward the connection portion.

9. The injection needle assembly according to claim 1, wherein the sticking needle tube is of 26 to 33 gauge.

10. The injection needle assembly according to claim 1, wherein the connection portion is elastically deformable.

11. The injection needle assembly according to claim 1, wherein the connection portion defines a first cross sectional area and the luminal portion defines a second cross sectional area, the second cross sectional area being less than the first cross sectional area.

12. The injection needle assembly according to claim 1, wherein the luminal portion of the connection portion is open on an outer circumferential surface thereof.

13. The injection needle assembly according to claim 12, wherein the needle holding portion includes a fitting portion, the connection portion being fitted into the fitting portion to thereby seal the open outer circumferential surface of the luminal portion in a liquid tight manner.

14. The injection needle assembly according to claim 1, wherein at least a portion of the connection portion is not hollow.

15. A medicine injection apparatus including:

an injector including an injection barrel filled with medicine and a needle tube, and an injection needle assembly attached to the injector, wherein the injection needle assembly includes:

a sticking needle tube having a needle tip to be stuck into a skin;

a needle holding portion for holding the sticking needle tube;

an engagement portion engaged with the injection barrel; and a connection portion which includes a luminal portion;

wherein a proximal end of the sticking needle tube, opposite to the needle tip of the sticking needle tube, is arranged in said luminal portion, an ejection port of the injector needle tube of the injector is arranged in said luminal portion, and said luminal portion of the connection portion thereby connects the sticking needle tube and the injector needle tube with each other in fluid communication in a liquid tight manner; wherein the needle holding portion further includes a fitting portion, the connection portion being fitted into the fitting portion to thereby seal an open outer circumferential surface of the luminal portion in a liquid tight manner.

16. The medicine injection apparatus according to claim 15, wherein the connection portion is elastically deformable.

17. The medicine injection apparatus according to claim 15, wherein the connection portion defines a first cross sectional area and the luminal portion defines a second cross sectional area, the second cross sectional area being less than the first cross sectional area.

18. The medicine injection apparatus according to claim 15, wherein the luminal portion of the connection portion is open on an outer circumferential surface thereof.

19. The medicine injection apparatus according to claim 15, wherein at least a portion of the connection portion is not hollow.

* * * * *